(12) United States Patent
Boiten

(10) Patent No.: US 11,801,152 B2
(45) Date of Patent: Oct. 31, 2023

(54) VALVE AND PROSTHETIC KNEE JOINT HAVING SUCH A VALVE

(71) Applicant: Ottobock SE & Co. KGaA, Duderstadt (DE)

(72) Inventor: Herman Boiten, Göttingen (DE)

(73) Assignee: Ottobock SE & Co. KGaA, Duderstadt (DE)

( * ) Notice: Subject to any disclaimer, the term of this patent is extended or adjusted under 35 U.S.C. 154(b) by 0 days.

(21) Appl. No.: 17/054,661

(22) PCT Filed: May 14, 2019

(86) PCT No.: PCT/EP2019/062366
§ 371 (c)(1),
(2) Date: Nov. 11, 2020

(87) PCT Pub. No.: WO2019/219697
PCT Pub. Date: Nov. 21, 2019

(65) Prior Publication Data
US 2021/0113354 A1    Apr. 22, 2021

(30) Foreign Application Priority Data

May 14, 2018   (DE) .................... 10 2018 111 441.9

(51) Int. Cl.
*A61F 2/64* (2006.01)
*A61F 2/74* (2006.01)
(Continued)

(52) U.S. Cl.
CPC ............... *A61F 2/64* (2013.01); *A61F 2/68* (2013.01); *F16K 11/07* (2013.01); *A61F 2/74* (2021.08); *A61F 2/744* (2021.08); *A61F 2/748* (2021.08)

(58) Field of Classification Search
CPC ..................................................... A61F 2/748
See application file for complete search history.

(56) References Cited

U.S. PATENT DOCUMENTS 3,818,926 A    6/1974  Wohlwend
3,921,665 A    11/1975 Lebzelter
(Continued)

FOREIGN PATENT DOCUMENTS

CN    101382200 A    3/2009
CN    103002836 A    3/2013
(Continued)

OTHER PUBLICATIONS

Japanese Patent Office; English Translation of Office Action in Japanese Patent Appl. No. 2020-563894; dated Jan. 4, 2022; 5 pages.
(Continued)

*Primary Examiner* — Jacqueline Woznicki
(74) *Attorney, Agent, or Firm* — WC&F IP

(57) ABSTRACT

A valve with an inlet, an outlet that is connected to the inlet via a fluid connection, and a valve body, which can be brought by displacing it along a displacement direction into a first position, in which the fluid connection is blocked, and a second position, in which the fluid connection is open, wherein the inlet is designed and arranged in such a way that a fluid entering through the inlet exerts a total force on the valve body that at least also acts in a force direction which is perpendicular to the displacement direction when the valve body is in the first position.

11 Claims, 6 Drawing Sheets

(51) Int. Cl.
*A61F 2/68* (2006.01)
*F16K 11/07* (2006.01)

(56) References Cited

U.S. PATENT DOCUMENTS

| | | | |
|---|---|---|---|
| 5,545,233 A | 8/1996 | Fitzlaff | |
| 5,704,945 A | 1/1998 | Wagner et al. | |
| 7,344,569 B2 | 3/2008 | Imakita et al. | |
| 9,402,748 B2 | 8/2016 | Boender | |
| 2005/0027270 A1 | 2/2005 | Cree et al. | |
| 2005/0027370 A1* | 2/2005 | Chen | A61F 2/644 623/44 |
| 2007/0173953 A1 | 7/2007 | Imakita et al. | |
| 2008/0302993 A1 | 12/2008 | Bigler | |
| 2010/0019347 A1 | 1/2010 | McLellan | |
| 2010/0191347 A1 | 7/2010 | Pusch | |
| 2012/0012768 A1 | 1/2012 | Yahr et al. | |
| 2012/0191219 A1 | 7/2012 | Boender | |
| 2016/0235558 A1* | 8/2016 | Boender | A61F 2/604 |
| 2021/0196483 A1* | 7/2021 | Boiten | A61F 2/64 |
| 2022/0175556 A1* | 6/2022 | Boiten | A61F 2/68 |

FOREIGN PATENT DOCUMENTS

| | | | | |
|---|---|---|---|---|
| DE | 4233247 A1 | 4/1994 | | |
| DE | 10 2007 032 090 A1 | 1/2009 | | |
| DE | 102007032090 A1 * | 1/2009 | | A61F 2/60 |
| DE | 102007032090 A1 | 1/2009 | | |
| DE | 10 2012 013 141 A1 | 5/2014 | | |
| EP | 2000714 A2 * | 12/2008 | | F16K 11/048 |
| EP | 2000714 A2 | 12/2008 | | |
| JP | 62-136669 U | 8/1987 | | |
| JP | H8-317944 A | 12/1996 | | |
| JP | H10-318426 A | 12/1998 | | |

OTHER PUBLICATIONS

International Search Report for International Application No. PCT/EP2019/062366, dated Jul. 17, 2019, 13 pages.

* cited by examiner

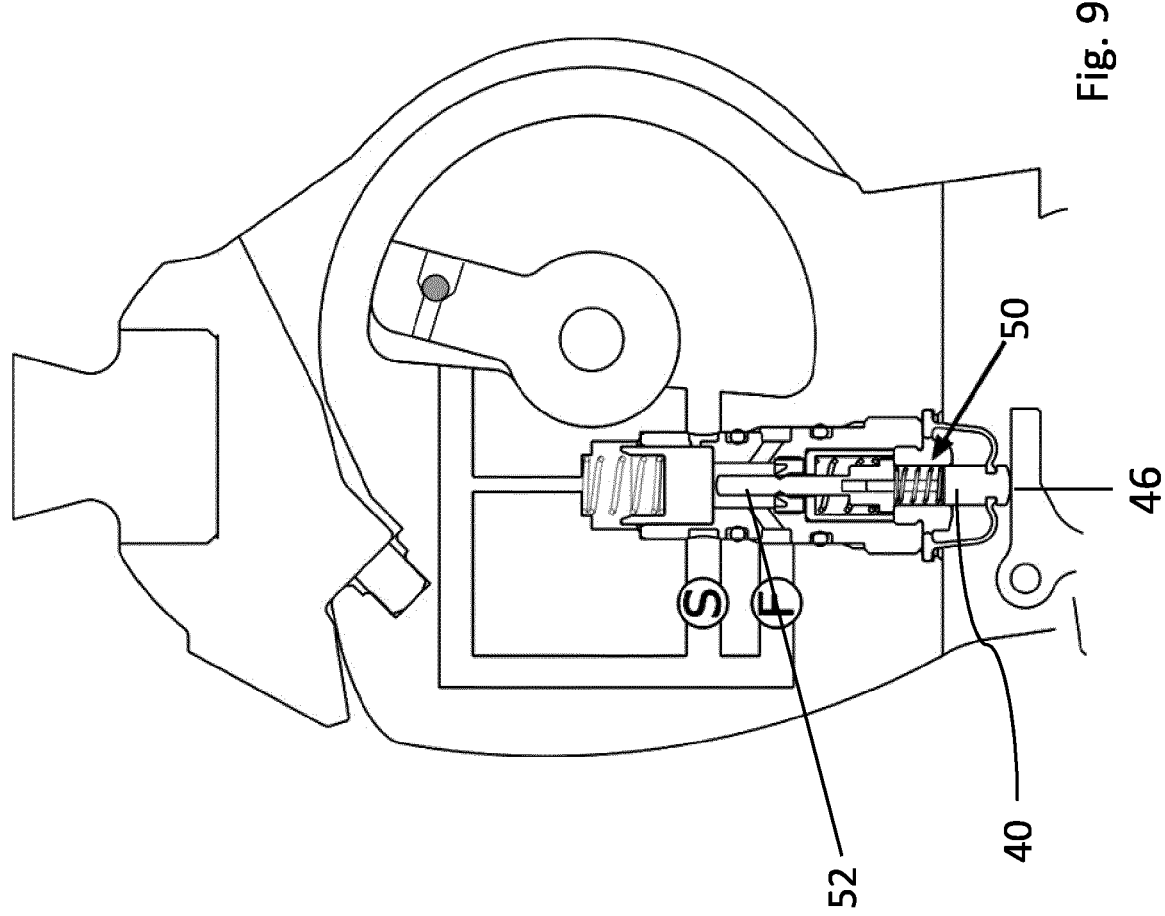

VALVE AND PROSTHETIC KNEE JOINT HAVING SUCH A VALVE

CROSS REFERENCE TO RELATED APPLICATIONS

This application is a U.S. National Entry and claims priority to PCT International Patent Application No. PCT/EP2019/062366, filed 14 May 2019, and entitled "VALVE AND PROSTHETIC KNEE JOINT HAVING SUCH A VALVE", which claims priority to Germany Patent Application No. 10 2018 111 441.9 filed 14 May 2018, the entire disclosures of which are incorporated herein by this reference.

TECHNICAL FIELD

The invention relates to a valve with an inlet, an outlet that is connected to the inlet by a fluid connection, and a valve body which can be brought into a first position, in which the fluid connection is blocked, by displacing it in a displacement direction, and into a second position, in which the fluid connection is open. The invention also relates to a prosthetic knee joint with this type of valve.

BACKGROUND

Prosthetic knee joints and hydraulic valves used alongside them have been known within the scope of the prior art for many years. Prosthetic knee joints should be damped to different degrees at different phases of a gait cycle. While a low degree of damping is required in the swing phase, a higher degree of damping is desirable in the standing phase. At the beginning of the standing phase, upon heel impact, the prosthetic knee is generally fully extended. In this case, it is important to counter-balance a possible flexion of the knee with a high degree of resistance so as to ensure that the prosthesis is stable and secure for the wearer when he is wearing and walking with it. However, this does not only apply to the fully extended state. For instance, if the wearer of the prosthesis trips, the fully extended state of the knee is generally not achieved before the foot lands on the ground. Nevertheless, in these cases in particular it is important to prevent an uncontrolled and too smooth a continued flexion of the knee, in order to prevent the wearer from falling.

To this end, U.S. Pat. No. 9,402,748 B2 for example describes a valve which only reduces the flow resistance in the fluid connection if a fully extended knee is detected alongside a load on the forefoot, i.e. a load in the toe area of the foot. While the load on the forefoot indicates that the next step in the gait cycle is the lifting of the foot from the floor, the so-called "toe-off", this is not sufficient as a single control parameter. An equivalent load on the forefoot may also occur, for instance, if the wearer of the prosthesis climbs a ramp or an incline and the forefoot is subjected to a load when in the bent state. In this case however, unlike with the initial swing phase, the damping of the knee joint absolutely cannot be reduced as this would cause the wearer to fall. The extension of the knee is thus detected as a second parameter.

Knees of this type with dual sensor technology are intricate, prone to errors and cost-intensive to produce. The different sensors must also either be supplied with electrical energy, which renders the construction of the knee large, cumbersome and heavy, or sensors must be used that can be operated without electricity, which are structurally intricate.

SUMMARY

The invention thus aims to develop a valve and a prosthetic knee joint which allow these disadvantages to be avoided or at least reduced. The invention solves the problem by way of a valve, wherein an inlet of the valve is designed and arranged such that a fluid entering through the inlet exerts a total force on the valve body that at least also acts in a force direction which is perpendicular to the displacement direction when the valve body is in the first position.

If such a valve is installed in a prosthetic knee joint, it may block a fluid connection between an extension chamber and a flexion chamber of the hydraulic system of the prosthetic knee joint, or at least reduce the flow. If the fluid connection in which the valve is installed refers to the fluid connection between the extension chamber and the flexion chamber of the prosthetic knee joint, this results in a complete blockage of the knee joint when the valve is closed, i.e. when the valve body is in the first position. There is preferably at least one additional fluid connection available which enables a flow of fluid from the extension chamber into the flexion chamber. To this end, a bore may be provided in a piston, such as a rotary piston, the movement of which guides fluid from one chamber into the other chamber. The passage is preferably equipped with a one-way valve to prevent a return flow of the fluid from the flexion chamber into the extension chamber.

If the wearer of the prosthetic knee joint attempts to move the knee when the valve is in this state, i.e. to swivel an upper leg section of the knee relative to a lower leg section of the knee, an increase in pressure occurs in one part of the hydraulic system of the prosthetic knee joint. Such a swivelling of the upper leg part of the knee relative to the lower leg part of the knee always results in a displacement of hydraulic fluid from the extension chamber into the flexion chamber or vice-versa. Given that this occurs via a fluid connection, in which the valve is situated, it is at least partially prevented by the valve, as long as the valve body is in the first position. The fluid thus enters the valve through the inlet; however, it cannot leave the valve, so that the fluid exerts a total force on the valve body. Conventionally, care is taken with valves to ensure that this total force exerted by the fluid does not comprise any components which do not run parallel to the displacement direction of the valve body. A hydrostatic bearing is thus achieved, which ensures a light and low-wear displacement of the valve.

A corresponding configuration is described, for instance, in U.S. Pat. No. 7,344,569 B2. In this case, for example, eight openings are provided, which are placed equidistant from one another across the circumference of the valve; via these openings, fluid which has entered the valve through the inlet comes into contact with the valve body. As a result, in this case a total force is applied to the valve body by the fluid, the total force comprising no components which are perpendicular to the displacement direction.

With a valve according to the invention, this aspect is fundamentally different. The fluid which has entered via the inlet exerts a total force on the valve body, the total force comprising a corresponding component which is perpendicular to the displacement direction.

The valve body preferably rests on a wall of a housing in this force direction. By way of the total force applied to the valve body by the fluid when the valve body is in the first position, the friction between the valve body and the wall of the housing on which it rests increases. This results in a holding force that counteracts a displacement of the valve body from the first position into the second position. This holding force then always occurs when the valve body is in the first position and the fluid exerts a total force on the valve body at the same time. This total force can only occur when a torque acts on the knee, i.e. when there is a force which wants to swivel a lower leg part of the prosthetic knee joint relative to an upper leg part of the prosthetic knee joint. However, this is only the case when the knee is not fully extended.

As a result of the configuration of a valve according to the invention, the sensor of a conventional prosthetic knee joint, which detects the extension of the knee, can be completely foregone. The entire system is therefore smaller, easier to produce and more cost effective.

The valve preferably features a previously described fluid connection between an extension chamber and a flexion chamber of the hydraulic system, which enables a flow of fluid from the extension chamber into the flexion chamber. To this end, a bore may be provided in a piston, such as a rotary piston, the movement of which guides fluid from one chamber into the other chamber. The passage is preferably equipped with a one-way valve to prevent a return flow of the fluid from the flexion chamber into the extension chamber.

The inlet is preferably designed such that incoming fluid flows towards the valve body along a section of its circumference which is smaller than 240°, preferably smaller than 210°, and greater than 120°, preferably greater than 150°. It is especially preferable if the section is 180°. For example, the inlet may be in the form of a slit that extends across the given section of the circumference of, for instance, a housing that encloses the valve body. Thanks to this configuration of the slit within an angular range, the desired total force is achieved on the opposite surface.

In a preferred configuration, the valve has a switch pin, the activation of which allows the valve body to be brought from the first position into the second position. This type of switch pin may be used, for instance, to displace the valve body from the first position into the second position, thereby opening the valve. This is only possible when the force applied by the switch pin is greater than the holding force to be overcome, said holding force being generated by the increase in friction, as a total force is exerted on the valve body by the fluid. In this case, a skilled selection of materials, geometries of the surfaces involved and the configuration of the valve can ensure that the valve can only be opened when there is no pressure or the pressure is very low, which is generally the case when the prosthetic knee joint is extended and no bending movement takes place.

Preferably the valve comprises a switch spring, which is configured to transfer a force from the switch pin to the valve body when the switch pin is activated. It is thus possible to create an upper limit for the force applied. In this case, it is important that the switch spring is located in the flux of the control. For example, it may be arranged as an interruption in the switch pin or switch lever or at another point in the flux between the lower part and the valve body. Regardless of the strength of the force applied to the switch pin, only a very limited force is transferred by the spring, at least in the short-term; thanks to a skilled selection of the spring constant, the type of spring and/or the spring material, said force is so small that it is not sufficient to open the valve, i.e. to displace the valve body from the first position into the second position, insofar as the pressure of the incoming fluid is greater than a predetermined limit, for example greater than 1 bar. This configuration is especially advantageous if even greater forces are able to act on the switch pins.

The spring is preferably selected such that the force transferred from the switch spring to the valve body is not sufficient to move the valve body from the first position into the second position when the valve body is subjected to a flow of fluid via the inlet, the fluid being at a pressure of 1 bar.

In a preferred embodiment, the valve body is spring-loaded towards the first position. Of course, it is thus possible to at least adjust the force that is required to move the valve body from the first position into the second position and thereby open the valve. In this case, it must be ensured that this force, which is generated by spring-loading the valve body towards the first position, is independent from the size of the pressure that is generated by the inflow of the fluid. The spring-loading is preferably produced by a spring, such as a helical spring, and in particular serves to close the valve when the movement of the joint reverses or fluid is not flowing through the valve.

The valve preferably comprises a throttle outlet, wherein the valve body is designed and arranged in such a way that fluid flowing in through the inlet at least also leaves the valve through the throttle outlet, regardless of the position of the valve body. This prevents the valve from being able to fully block a hydraulic connection or a hydraulic line into which it is inserted. It is only when the valve is closed, i.e. when the valve body is in the first position, that there is greater flow resistance to the fluid than when the valve is open, when the valve body is in the second position. The strength of the flow resistance is preferably adjustable. This means that it can be adjusted to fit the wearer of the prosthesis, for example to allow him to comfortably and conveniently climb stairs.

The invention also solves the problem by way of a prosthetic knee joint with a hydraulic arrangement that features an extension chamber, a flexion chamber and a valve as described here, wherein the inlet of the valve is connected to the flexion chamber and the outlet of the valve is connected to the extension chamber. If this type of prosthetic knee joint is bent, the hydraulic fluid flows from the flexion chamber into the extension chamber. The flexion chamber is thus connected to the inlet of the valve. As a result, the valve cannot be opened, i.e. the valve body cannot be displaced from the first position into the second position, as long as the knee that is subjected to a load is not completely or at least almost completely extended. In this case, the torque generated causes a pressure to be exerted on the fluid in the flexion chamber, said pressure translating into a total force on the valve body within the valve.

In a preferred configuration of the prosthetic knee joint, the prosthetic knee joint has a lower part, which can be connected to a lower leg. The lower part has a first component and a second component, which are mounted to each other so that they can swivel about a control axis. The lower part also has a switch mechanism, which is designed and arranged in such a way that the switch pin of the valve is activated when a force acts on the lower part, the pitch line of which extends in front of the control axis. Such a force only occurs when the forefoot of a prosthetic foot, which is arranged below the prosthetic knee joint, is subjected to a load. This configuration enables a prosthetic knee joint that can be controlled entirely without electronic components, said prosthetic knee joint being brought from a closed state, in which it counterbalances the hydraulic fluid by way of increased flow resistance, into an open state as soon as the forefoot is subjected to a load, and the pressure of the fluid in the flexion chamber is so low that the holding force between the valve body and the housing wall of the valve can be overcome. This enables the knee joints, which are only realised electronically in the prior art, without any electronic components.

BRIEF DESCRIPTION OF THE DRAWINGS

In the following, an example of an embodiment of the present invention will be explained in more detail by way of the attached figures: They show FIGS. 1, 3, 5 and 7—schematic sectional views through a prosthetic knee joint in various situations, FIGS. 2, 4, 6 and 8—enlarged sections from the respective preceding figures, FIG. 9—the schematic representation of the further embodiment of the present invention and FIGS. 10-11—schematic views of a valve according to an example of an embodiment of the present invention.

DETAILED DESCRIPTION

Figure 1:
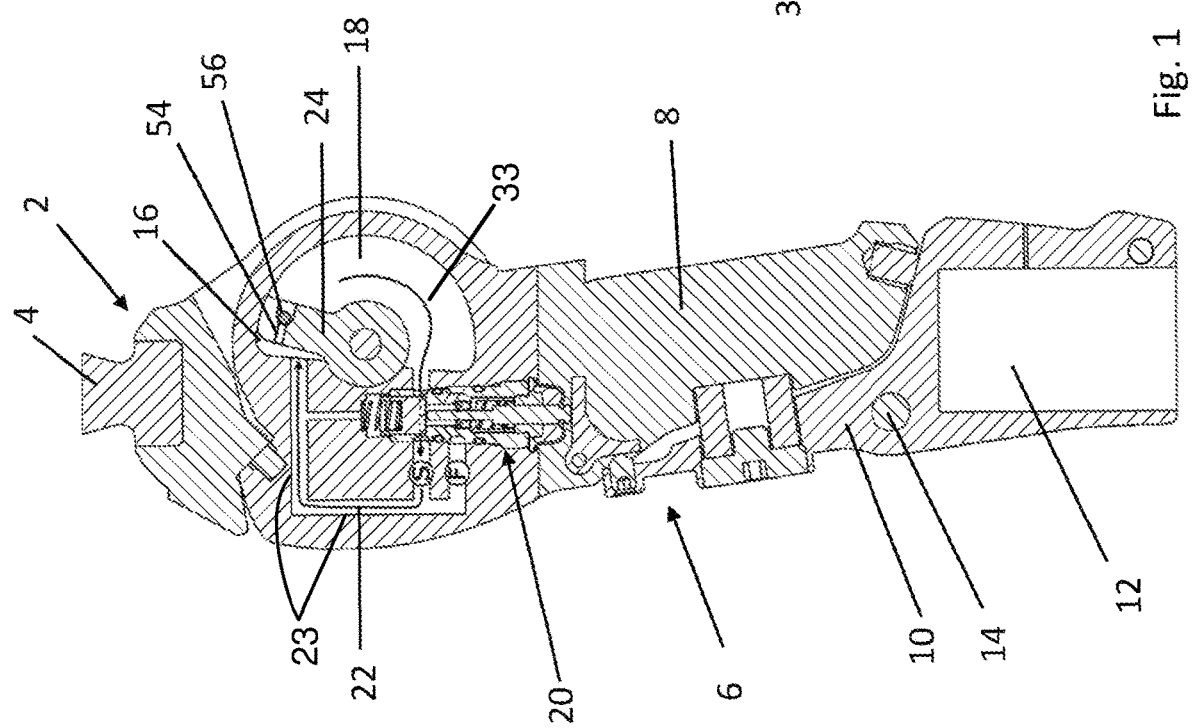

FIG. 1 depicts a sectional view through a prosthetic knee joint according to a first example of an embodiment of the present invention. It comprises an upper part 2 with an upper fixing element 4, on which, for example, a prosthesis shaft or another prosthetic component can be arranged. The upper part 2 is arranged on a lower part 6 such that it can be swivelled, said lower part comprising a first component 8 and a second component 10, which features a lower fixing element 12 that is designed as a tube clamp for a lower leg tube in the example of an embodiment shown. The first component 8 is arranged on the second component 10 such that it can be swivelled about a control axis 14.

In the prosthetic knee joint there is a hydraulic arrangement with an extension chamber 16, a flexion chamber 18 and a valve 20, which is arranged in a fluid connection 22 through one or more fluid channels 23. The extension chamber 16 is connected to the flexion chamber 18 by means of fluid connection 22. The extension chamber 16 is separated from the flexion chamber 18 by a piston 24, which moves in the volume, formed by the extension chamber 16 and the flexion chamber 18, when the knee is moved, i.e. the upper part 2 is swivelled relative to the lower part 6. As a result, fluid in the hollow space is guided from the extension chamber 16 into the flexion chamber 18 or vice-versa. In the example of an embodiment shown, a bore 54 is shown in the piston 24, wherein a non-return valve 56 is situated inside the bore. This bore 54 represents an additional fluid connection between the extension chamber 16 and the flexion chamber 18, which allows for a flow of fluid from the extension chamber 16 into the flexion chamber 18 but prevents such a flow in the opposite direction. In the figures shown, the position of the schematically depicted non-return valve 56 does not correspond to the actual position, but rather should serve only to illustrate the arrangement of the non-return valve 56.

Figure 2:
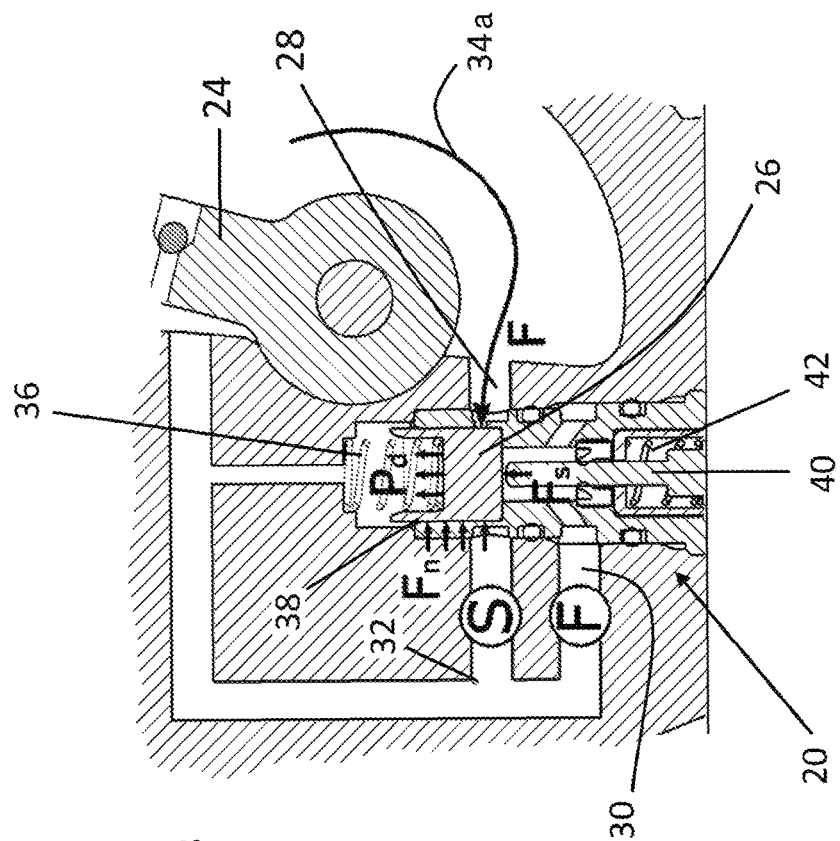

FIG. 2 depicts an enlarged section. The valve 20 features a valve body 26, which is in the first position in the situation shown in FIG. 2. The valve comprises an inlet 28, a first outlet 30 and a second/throttle outlet 32. A hydraulic fluid that enters the valve through the inlet 28 along the arrow 34a cannot leave the valve through the outlet 30, as the valve body 26 is in the first position. In this position it is spring-loaded by a spring 36. However, in the example of an embodiment shown the fluid can pass through the valve body 26 along a (second) fluid connection/pathway 33 (see FIGS. 1 and 8) and leave the valve through the throttle outlet 32. A clockwise swivelling of the piston 24 is consequently opposed by a large flow resistance.

The fluid that enters the valve through the inlet 28 strikes the valve body 26 and exerts a total force on this valve body 26, said force at least also comprising one component which is perpendicular to a displacement direction, along which the valve body 26 can be displaced. In the representations shown, the displacement direction extends from top to bottom. The total force applied results in a counter force $F_n$, which acts on an opposite side, on which the valve body 26 rests on a housing wall 38. The valve 20 also features a switch pin 40, which can exert a switch force $F_s$ on the valve body 26 from below in the example of an embodiment shown in order to displace said valve body from the first position depicted into the second position. Due to the static friction, the counter force $F_n$ generates a frictional force $F_r$, which is a result of the product of the counter force $F_n$ and the static force coefficients $\mu$.

A feedback spring 42 is arranged about the switch pin, said feedback spring being used to bring the switch pin 40 back into the starting position following the completion of a switch cycle.

Figure 3:
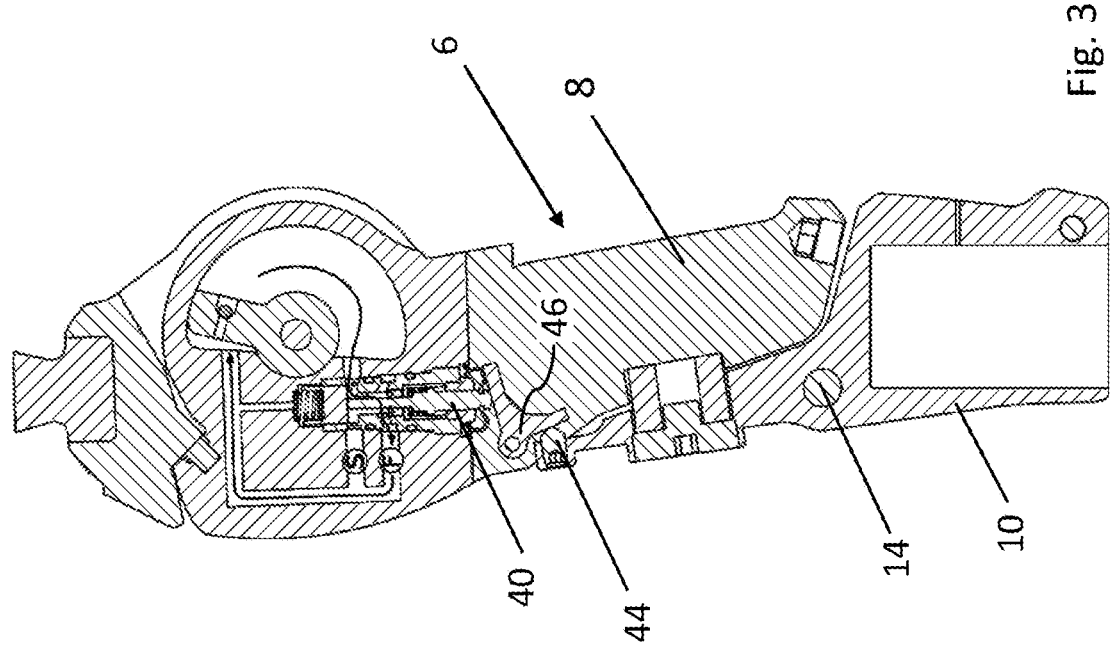

FIG. 3 shows the prosthetic knee joint from FIG. 1 in a second situation. Due to, for example, a load on the forefoot, i.e. a force acting on the lower part 6, whose pitch line lies in front of the control axis 14, i.e. left of the control axis 14 in the example of an embodiment shown, the first component 8 is swivelled about the control axis 14 relative to the second component 10. In this case, a switch lever 46 is moved by way of a switch screw 44, the switch lever striking the switch pin 40 from below and thereby transferring a switch force to the switch pin 40.

Figure 4:
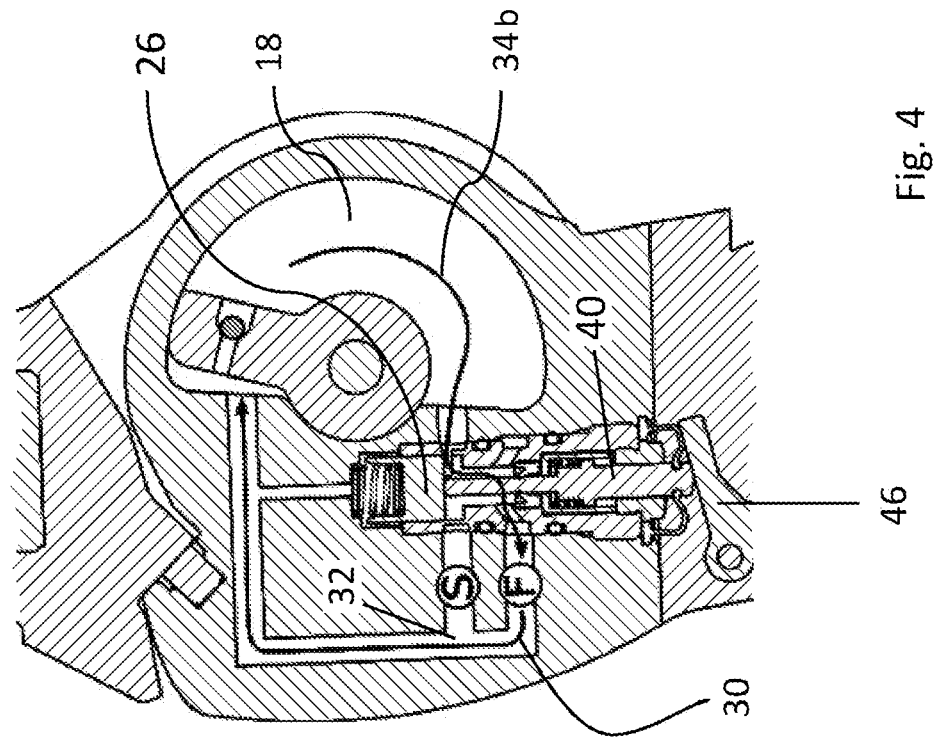

FIG. 4 depicts an enlarged section. The switch lever 46, which has displaced the switch pin 40 upwards, is clearly recognizable, which has caused the valve body 26 to be displaced from the first position, which was depicted in FIGS. 1 and 2, into the second position. The fluid can now flow out of the flexion chamber 18, along the (first) fluid connection/pathway 34b, and through the valve, and leave the valve not only through 25 the throttle outlet 32, but also through the outlet 30. The damping resistance that opposes the fluid is thus considerably lower than in the situation in FIGS. 1 and 2.

Figure 5:
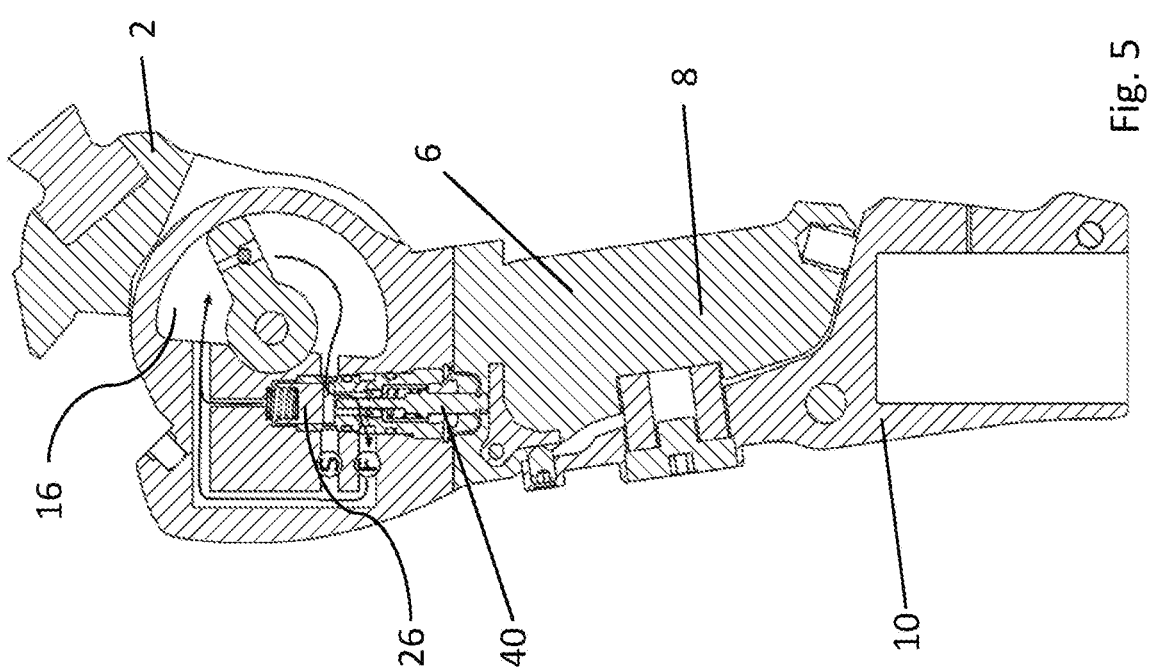

FIG. 5 shows the prosthetic knee joint in another situation. It is clear that the upper part 2 has been swivelled relative to the lower part 6. The extension chamber 16 is considerably larger. However, the first component 8 is no longer swivelled relative to the second component 10 of the lower part 6 and the switch pin 40 has returned to its original position. Nevertheless, the valve body 26 remains in the second position.

Figure 6:
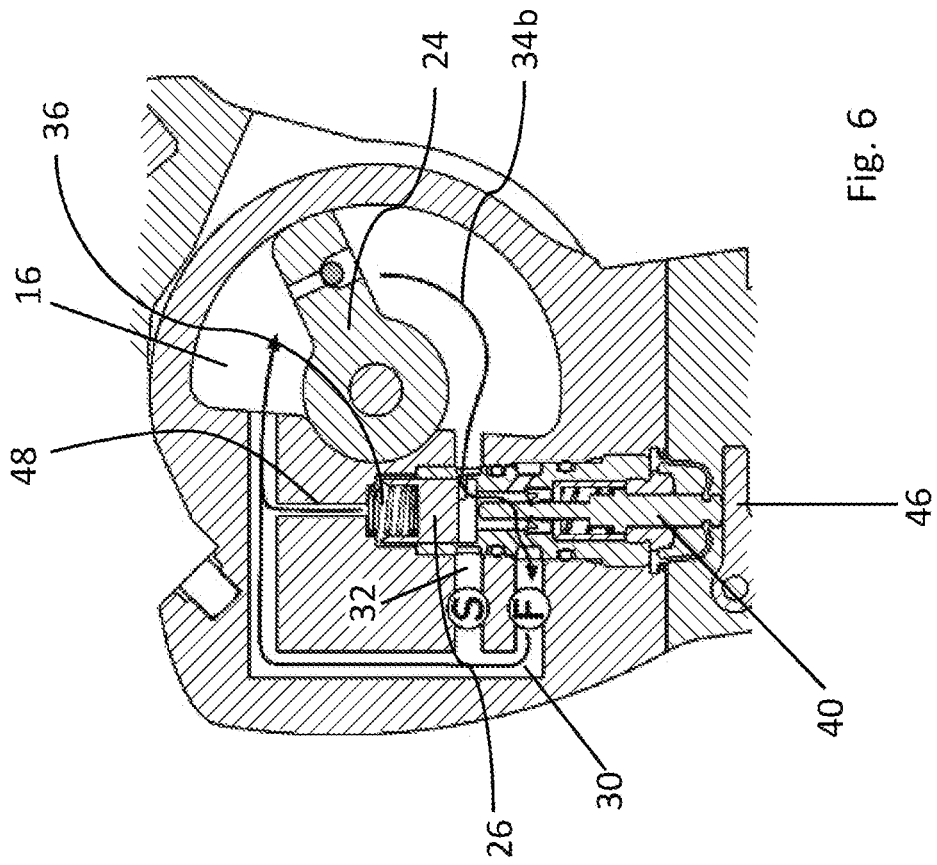

FIG. 6 depicts an enlarged section. The switch lever 46 has returned to the position from FIG. 1 and the switch pin 40 is no longer in contact with a lower side of the valve body 26. However, the swivelling of the upper part 2 relative to the lower part 6 of the prosthetic knee joint results in a swivelling of the piston 24, which causes fluid to be pushed through the valve along the first fluid connection/pathway 34b. An overpressure occurs inside the valve 20, as a flow resistance is produced by the outlet 30 and the throttle outlet 32.

A connection channel 48 is situated above the spring 36, said channel connecting the volume in which the spring 36 is located to the extension chamber 16. This area exhibits a negative pressure of the hydraulic fluid. Given that there is an overpressure below the valve body 26 and a negative pressure above the valve body 26, the valve body 26 is also held in the second position, shown in FIGS. 5 and 6, against the spring pressure of the spring 26, even if the switch force $F_s$ applied by the switch pin 40 is no longer there. The flexion of the knee is consequently only possible with a relatively low flow resistance and thus low damping.

Figure 7:
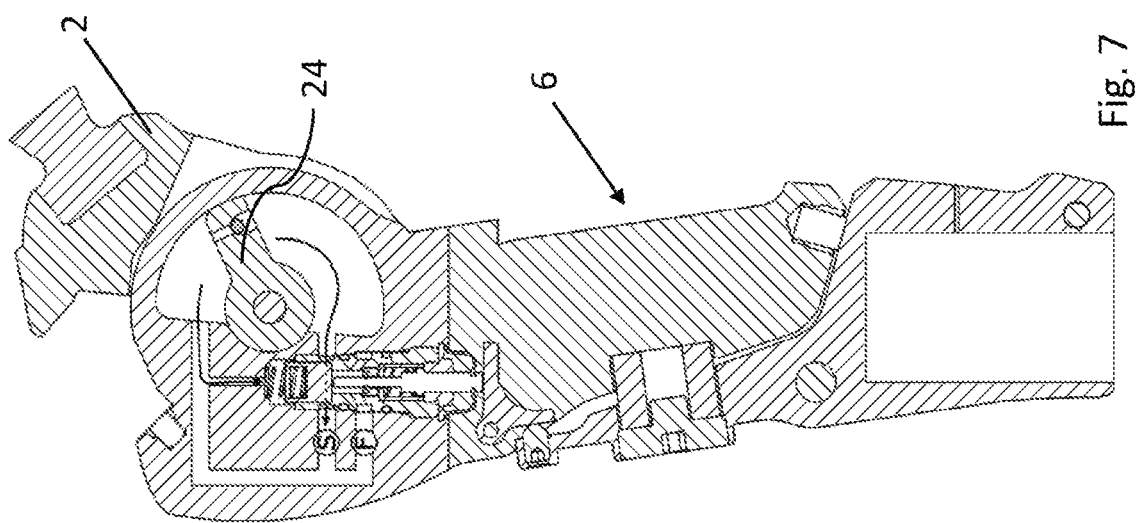

FIG. 7 shows the situation during the reversal of movement. In this case, the upper part 2 should be swivelled relative to the lower part 6 in such a way that the knee is extended. This results in an anti-clockwise movement of the piston 24.

Figure 8:
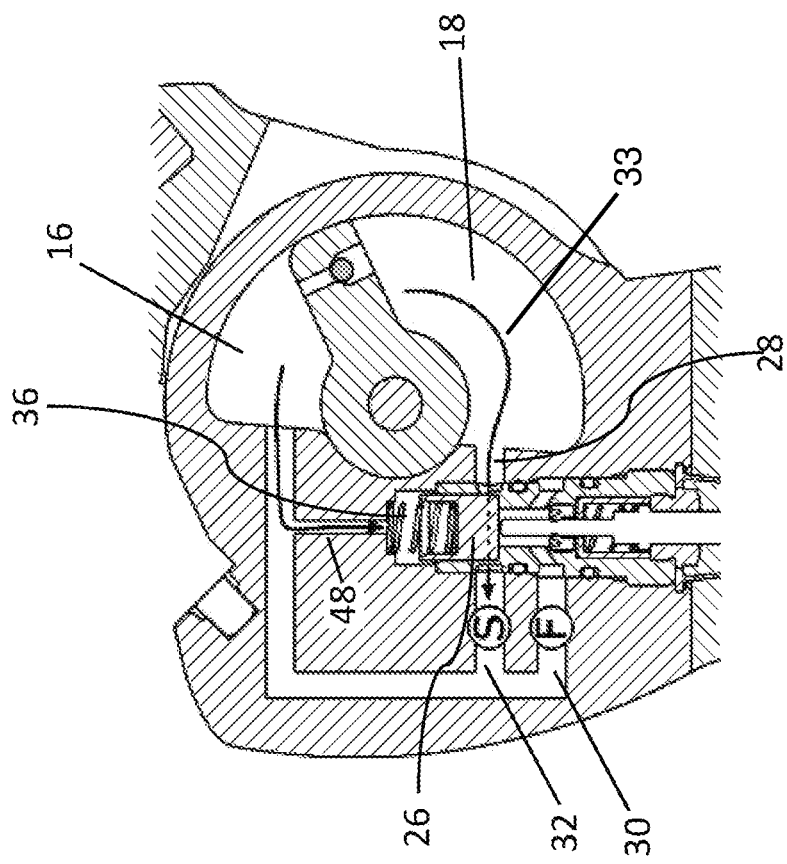

FIG. 8 shows an enlarged section, from which it is clear that, due to the overpressure in the extension chamber 16 caused by the reversal of movement, this pressure is also transferred via the connection channel 48 into the volume in which the spring 36 is located. As a result, the pressure situation shown in FIG. 6, which ensures that the valve body 26 remains in the depicted second position, is no longer applicable. Rather, the spring 36 and the overpressure applied via the connection channel 48 push the valve body 26 back into the first position, in which fluid can no longer enter the valve through the outlet 30, but rather only through the throttle outlet 32, wherein the fluid leaves said valve through the inlet 28 and enters the flexion chamber 18.

FIG. 9 depicts an enlarged section of the valve arrangement. In particular, a switch spring 50 is depicted, which is arranged between the switch pin 40 and a transmission pin 52. The switch lever 46 strikes the switch pin 40, which moves as a result. However, this movement is not immediately transferred to the valve body 26, but rather is initially transferred from the switch pin 40 to the switch spring 50. This initially transfers the switch force to the transmission pin 52 and hence to the valve body 26.

By selecting the spring constant of the switch spring 50, the force has an upper limit, at least in the short term. The force that can be applied to the valve body 26 via the switch spring 50 to switch the valve is selected in such a way that it is enough to overcome the spring pressure Pa and to displace the valve body 26 out of the first position depicted into the second position when there is no or only a very small counter force $F_n$. However, if a total force is exerted on the valve body 26 by the incoming fluid and the counter force $F_n$ thus produced, the switch force $F_s$, which is transferred to the valve body 26 by the switch spring 50 and the switch pin 40, is not sufficient to switch the valve.

Figure 11:
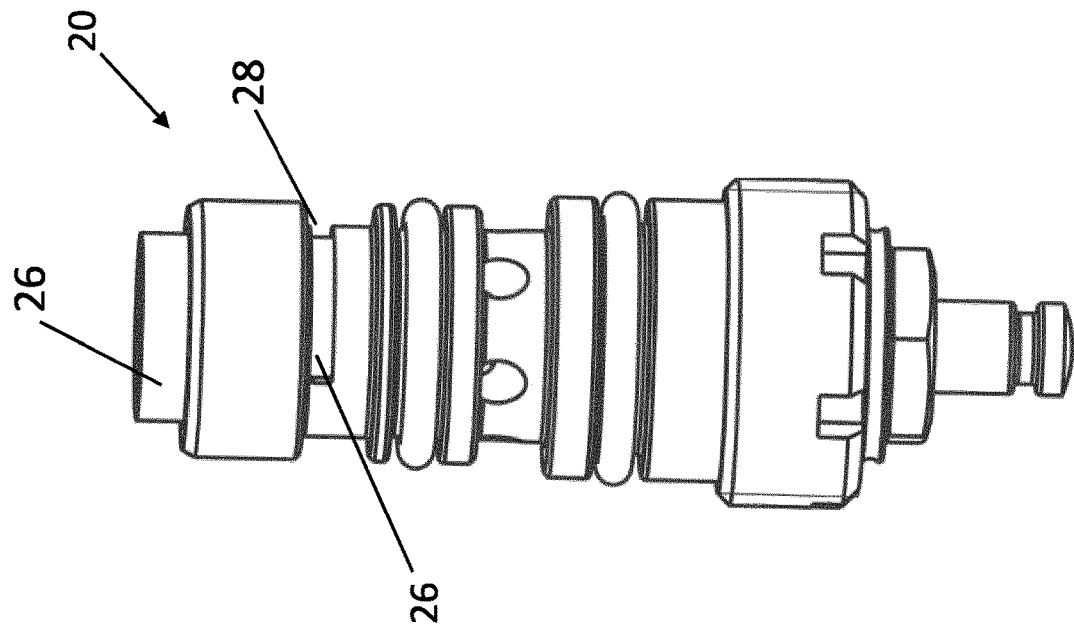
Figure 10:
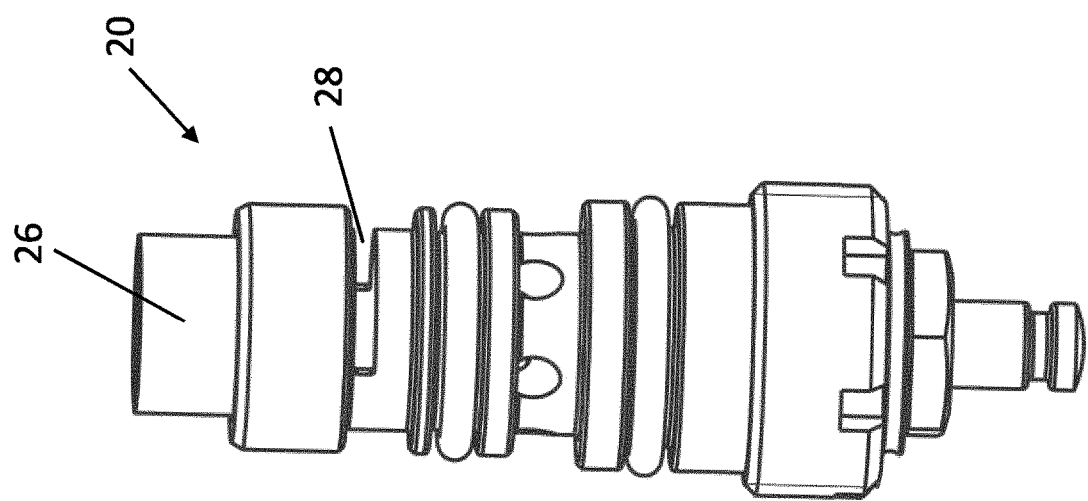

FIGS. 10 and 11 show an isolated image of the valve 20. Whereas the valve body 26 in the image in FIG. 10 is in the second position and the inlet 28 is therefore free, this is not the case in FIG. 11. The valve body 26 is in the first position, meaning that a fluid entering the valve 20 through the inlet 28 strikes the valve body 26 and exerts a force. It is clear that the inlet 28 covers a section of the circumference of the valve and thus also the valve body 26, said section being smaller than 180° in the example of an embodiment shown.

I claim:

1. A prosthetic knee joint comprising:
   a hydraulic arrangement that comprises:
   an extension chamber;
   a flexion chamber;
   a valve comprising:
     an inlet;
     a first outlet that is connected to the inlet via a first fluid connection;
     a second outlet which is a throttle outlet; and
     a valve body configured to be displaced along a displacement direction into a first position and a second position, the valve body connecting the second outlet to the inlet via the valve body,
   wherein in the first position the first fluid connection between the inlet and the first outlet is blocked and a second fluid connection between the inlet and the second outlet through the valve body is open,
   wherein in the second position the first fluid connection between the inlet and the first outlet is open and the second fluid connection between the inlet and the second outlet is open,
   wherein the inlet is configured and arranged in such a way that a fluid entering through the inlet exerts a total force on the valve body that at least also acts in a force direction which is perpendicular to the displacement direction when the valve body is in the first position;
   wherein the inlet of the valve is connected to the flexion chamber and each of the first outlet and the second outlet of the valve is connected to the extension chamber.

2. The prosthetic knee joint according to claim 1, further comprising a housing containing the hydraulic arrangement and comprising a housing wall, and wherein the valve body rests on the housing wall in the force direction.

3. The prosthetic knee joint according to claim 1, wherein the inlet is configured such that the fluid flows towards the valve body along a section of its circumference which is smaller than 240°.

4. The prosthetic knee joint according to claim 1, wherein the valve further comprises a switch pin, the activation of which enables movement of the valve body from the first position into the second position.

5. The prosthetic knee joint according to claim 4, wherein the valve further comprises a switch spring which is configured to transfer a force from the switch pin to the valve body when the switch pin is activated.

6. The prosthetic knee joint according to claim 5, wherein the switch spring is selected such that the force transferred from the switch spring to the valve body is not sufficient to move the valve body from the first position into the second position when the valve body is subjected to the fluid via the inlet, the fluid being at a pressure of about 1 bar.

7. The prosthetic knee joint according to claim 4, further comprising an upper part and a lower part,
   wherein the valve further comprises a switch spring,
   wherein the switch pin is activated when a first force acts on the lower part,
   wherein the switch spring is configured to transfer a second force from the switch pin to the valve body when the switch pin is activated, and
   wherein the second force is less than the first force.

8. The prosthetic knee joint according to claim 4, further comprising a lower part with a first component and a second component which are mounted to one another such that the first component and the second component are able to be swivelled about a control axis, and
   wherein the switch pin of the valve is activated when a force acts on the lower part, said force extending in front of the control axis.

9. The prosthetic knee joint according to claim 1, wherein the valve body is spring-loaded towards the first position.

10. The prosthetic knee joint according to claim 1, wherein the valve body is designed and arranged in such a way that the fluid flowing in through the inlet is able to leave the valve at least through the second outlet, regardless of whether the valve body is in the first position or the second position.

11. A prosthetic knee joint comprising:
   an extension chamber;
   a flexion chamber;
   a valve comprising:
     an inlet by which fluid from the extension chamber enters the valve, a first outlet for fluid to leave the valve,
a second outlet for fluid to leave the valve, wherein the second outlet is a throttle outlet, and
a valve body configured to be displaced along a displacement direction into a first position and a second position;
a first fluid pathway which extends from the inlet to the first outlet;
a second fluid pathway which extends from the inlet to the second outlet;
one or more fluid channels permitting fluid which leaves the first or second outlet to flow to the extension chamber;
wherein the inlet is configured and arranged such that fluid entering through the inlet exerts a total force on the valve body that at least also acts in a force direction which is perpendicular to the displacement direction when the valve body is in the first position,
wherein the first fluid pathway is (i) blocked when the valve body is in the first position and (ii) open when the valve body is in the second position, and
wherein the second fluid pathway is open regardless of whether the valve body is in the first position or the second position.

* * * * *